(12) United States Patent
Murai

(10) Patent No.: US 11,259,755 B2
(45) Date of Patent: Mar. 1, 2022

(54) TERMINAL DEVICE, INFORMATION PROVIDING SYSTEM, AND COMPUTER PROGRAM

(71) Applicant: PARAMOUNT BED CO., LTD., Tokyo (JP)

(72) Inventor: Shinya Murai, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 415 days.

(21) Appl. No.: 16/323,131

(22) PCT Filed: Nov. 21, 2017

(86) PCT No.: PCT/JP2017/041834
§ 371 (c)(1),
(2) Date: Feb. 4, 2019

(87) PCT Pub. No.: WO2018/097133
PCT Pub. Date: May 31, 2018

(65) Prior Publication Data
US 2019/0159738 A1 May 30, 2019

(30) Foreign Application Priority Data
Nov. 22, 2016 (JP) .............................. JP2016-227222

(51) Int. Cl.
*A61B 5/00* (2006.01)
*G16H 40/67* (2018.01)
(Continued)

(52) U.S. Cl.
CPC .............. *A61B 5/742* (2013.01); *G06F 11/07* (2013.01); *G06Q 50/22* (2013.01); *G16H 15/00* (2018.01);
(Continued)

(58) Field of Classification Search
CPC .......... A61B 5/742; G06F 11/07; G16H 40/20; G16H 40/63; G16H 40/67; G16H 15/00; G16H 10/60; G06Q 50/22
See application file for complete search history.

(56) References Cited

U.S. PATENT DOCUMENTS

| | | | |
|---|---|---|---|
| 9,621,507 B2 * | 4/2017 | Wang | H04L 67/26 |
| 2014/0039446 A1 * | 2/2014 | Day | G16H 40/40 |
| | | | 604/500 |
| 2016/0278706 A1 * | 9/2016 | Okamoto | A61B 5/0013 |

FOREIGN PATENT DOCUMENTS

| | | | |
|---|---|---|---|
| JP | 2002-041671 A | 2/2002 |
| JP | 2010-022678 A | 2/2010 |

(Continued)

OTHER PUBLICATIONS

Cernich, Alison N., David M. Brennana, Linsey M. Barker, Joseph Bleiberg. "Sources of error in computerized neuropsychological assessment." Archives of Clinical Neuropsychology 22S (2007) S39-S48 (Year: 2007).*

(Continued)

*Primary Examiner* — Linh Giang Le
(74) *Attorney, Agent, or Firm* — Birch, Stewart, Kolasch & Birch, LLP

(57) ABSTRACT

This terminal device is provided with: an acquisition unit which receives, from a server, information displayed on a display device used for medical treatment or care, and stores the received information in a storage unit; and a display control unit which displays the information on the display device. When a display stop condition, which indicates the likelihood that there is a difference between information stored in the server and information stored in the storage unit, is satisfied, the display control unit stops the display of at least information about biological information on a facil- (Continued)

ity user who is a person requiring the medical treatment or care, among the information on the display device.

17 Claims, 9 Drawing Sheets

(51) Int. Cl.
  *G16H 15/00* (2018.01)
  *G06F 11/07* (2006.01)
  *G16H 40/20* (2018.01)
  *G06Q 50/22* (2018.01)
  *G16H 40/63* (2018.01)
  *G16H 10/60* (2018.01)

(52) U.S. Cl.
  CPC ............. *G16H 40/20* (2018.01); *G16H 40/63* (2018.01); *G16H 40/67* (2018.01); *G16H 10/60* (2018.01)

(56) References Cited

FOREIGN PATENT DOCUMENTS

| | | |
|---|---|---|
| JP | 2011-103055 A | 5/2011 |
| JP | 2012-118782 A | 6/2012 |
| JP | 2016-139224 A | 8/2016 |
| JP | 2016-181133 A | 10/2016 |
| KR | 101522401 B1 * | 5/2015 |
| WO | WO 2011-011454 A1 | 1/2011 |
| WO | WO 2011-127459 A1 | 10/2011 |
| WO | WO 2012-088535 A1 | 8/2012 |
| WO | WO 2014-158133 A1 | 10/2014 |

OTHER PUBLICATIONS

International Search Report for PCT/JP2017/041834 (PCT/ISA/210) dated Jan. 30, 2018.

* cited by examiner

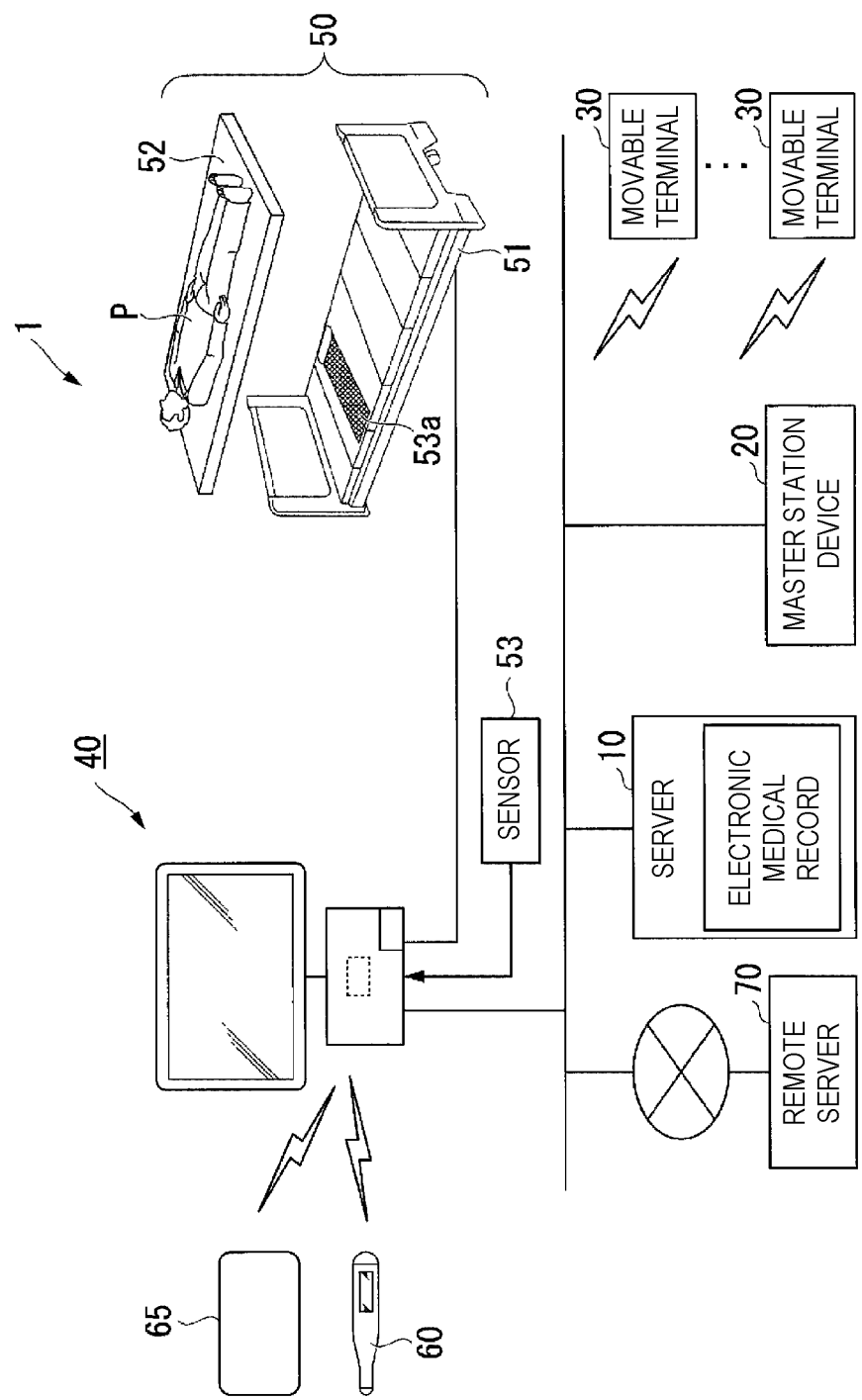
[Fig. 1]

[Fig. 2]
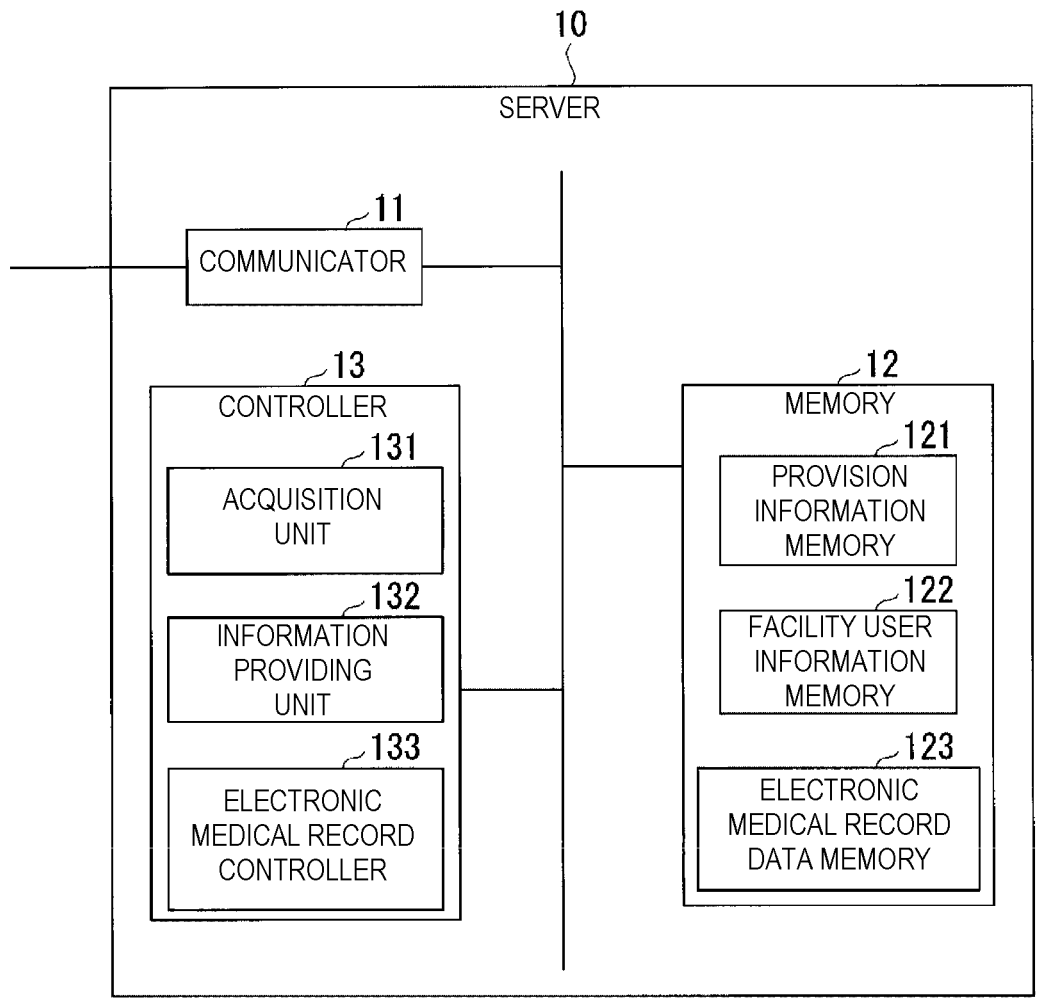
[Fig. 3]
| FACILITY USER IDENTIFICATION INFORMATION | USER INTERFACE DEVICE IDENTIFICATION INFORMATION | ATTRIBUTE INFORMATION | |
|---|---|---|---|
| | | | ~71 |
| | | | |
| | | | |
| | | | |

[Fig. 4]

| | 81 | 82 | 83 |

FACILITY USER IDENTIFICATION INFORMATION:
NAME:
DOCTOR IN CHARGE:
DOCTOR ATTENDING:
NURSE IN CHARGE:
DIAGNOSIS AND TREATMENT DEPARTMENT:
SICKROOM NUMBER:
BED NUMBER:

REGULAR COLLECTION OF BLOOD

BEDSORE CAUTION

PROHIBITION OF NOSE BLOWING

USE OF AIR MATTRESS

...

| MEASUREMENT DATE/TIME | PULSE | SYSTOLIC BLOOD PRESSURE | DIASTOLIC BLOOD PRESSURE | BODY TEMPERATURE |
|---|---|---|---|---|
| 2016/4/2 13:21 | 108 | 143 | 101 | 36.8 |
| ... | ... | ... | ... | ... |

[Fig. 5]
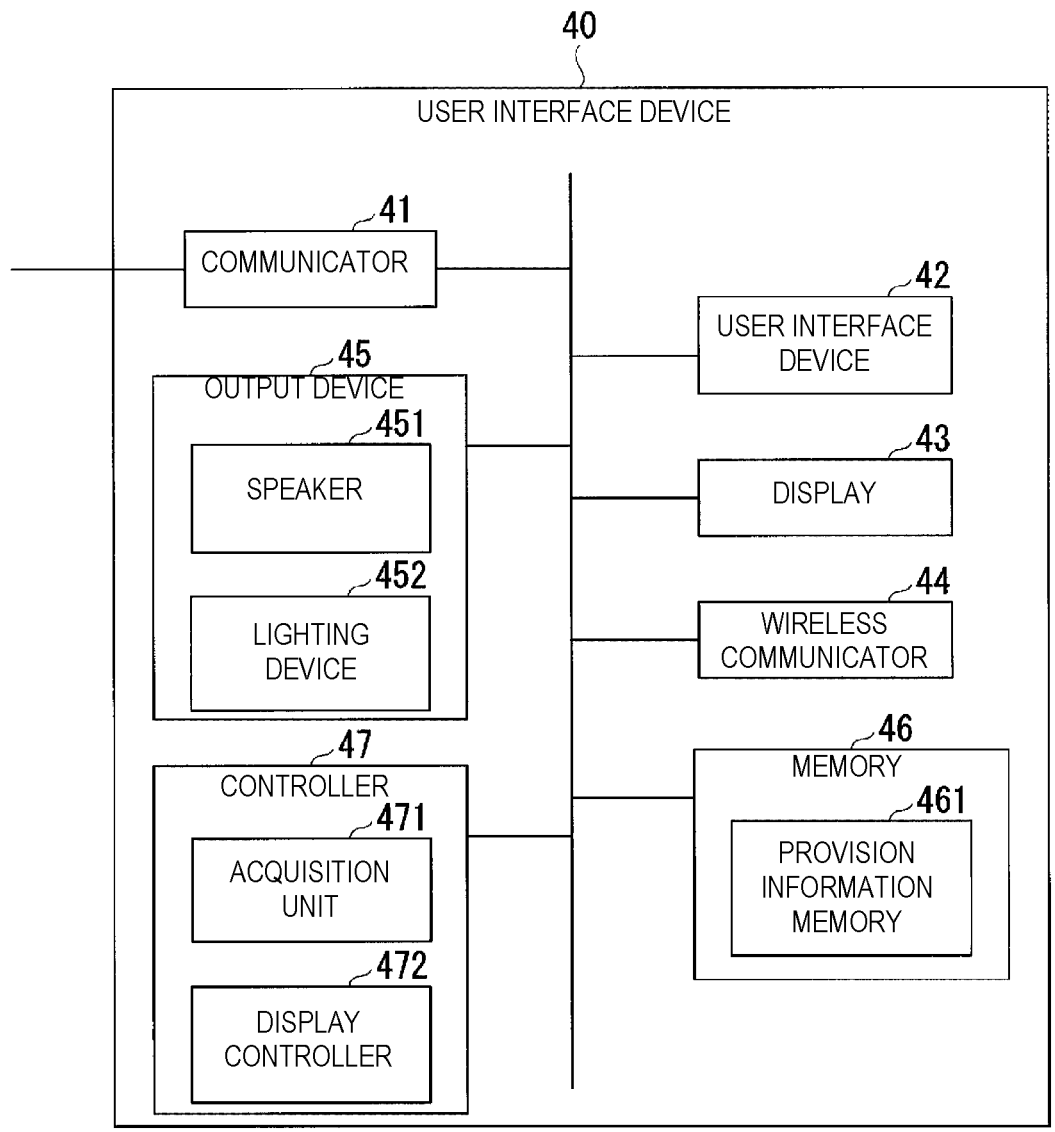

[Fig. 6]
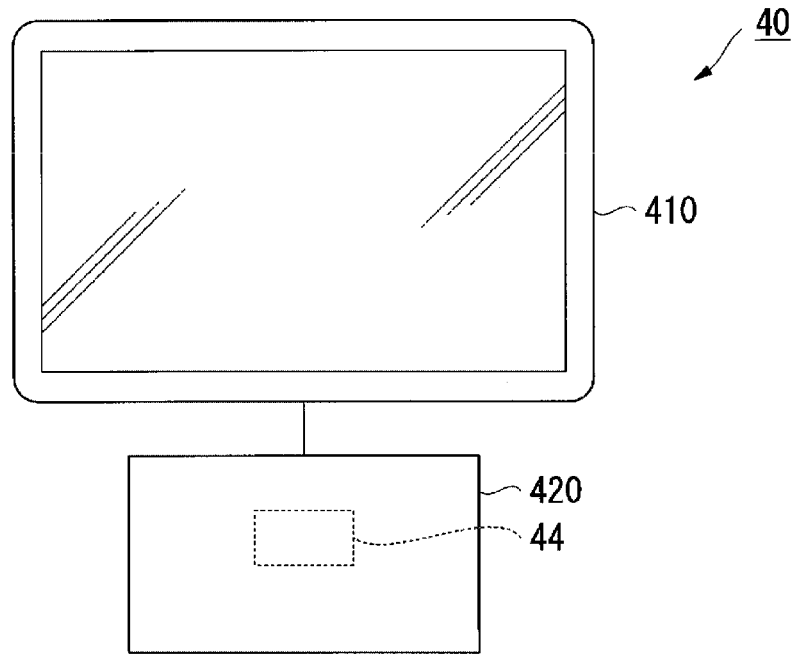
[Fig. 7]
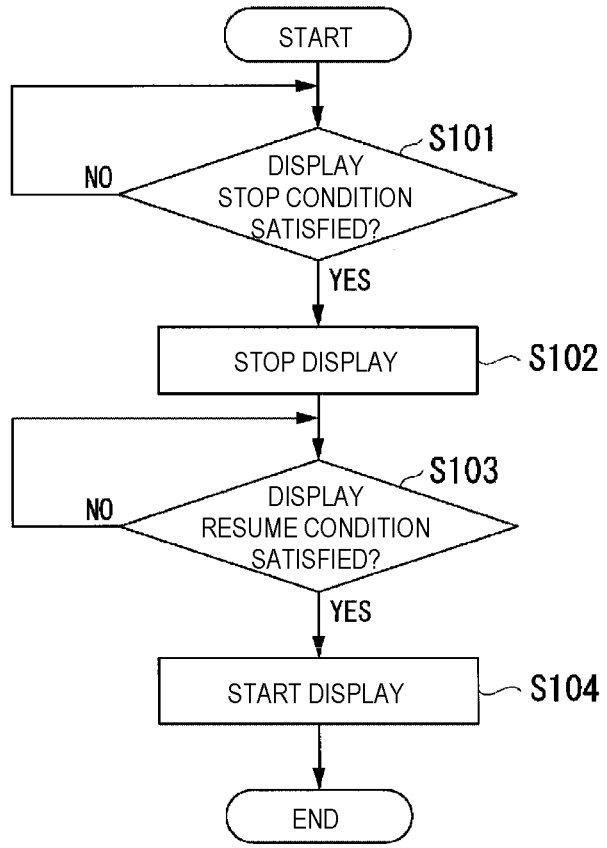

[Fig 8]
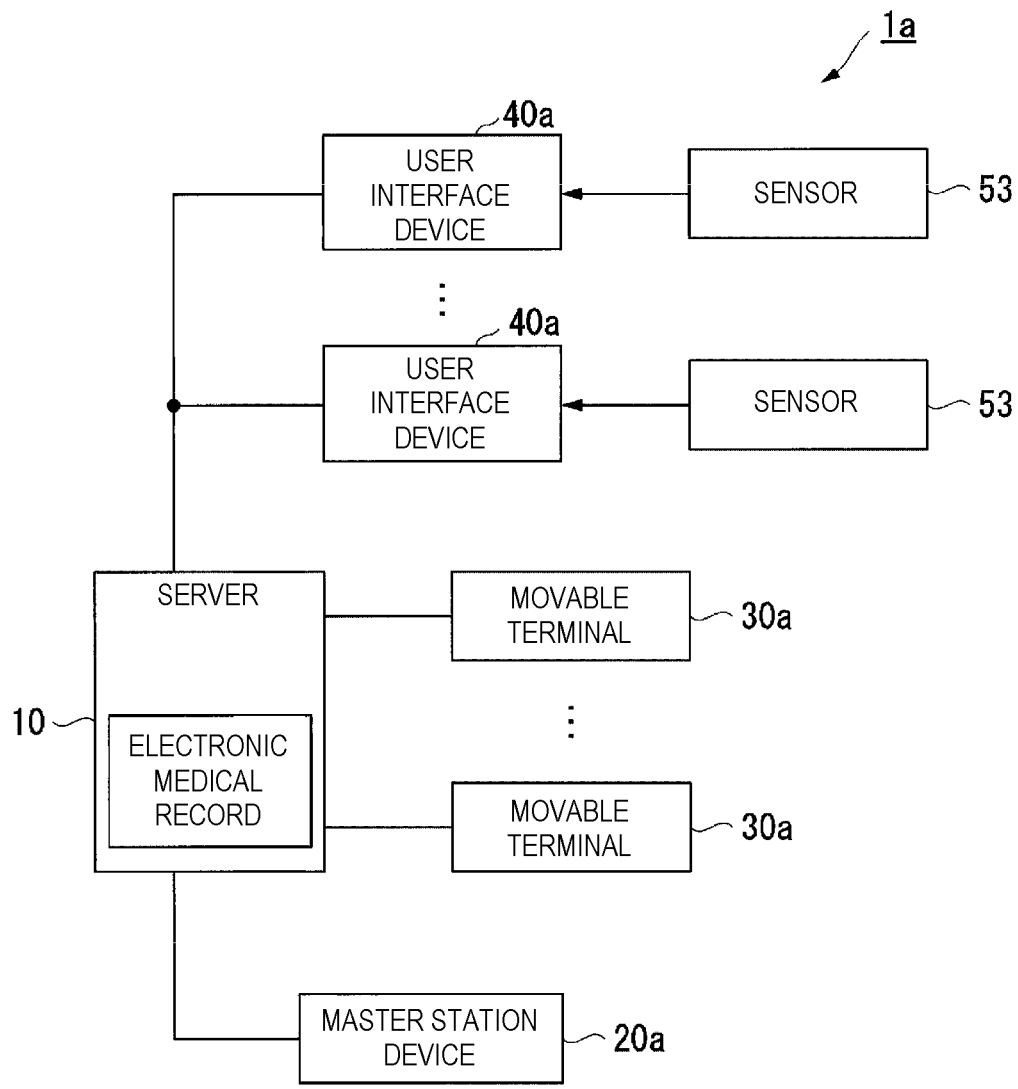

[Fig. 9]
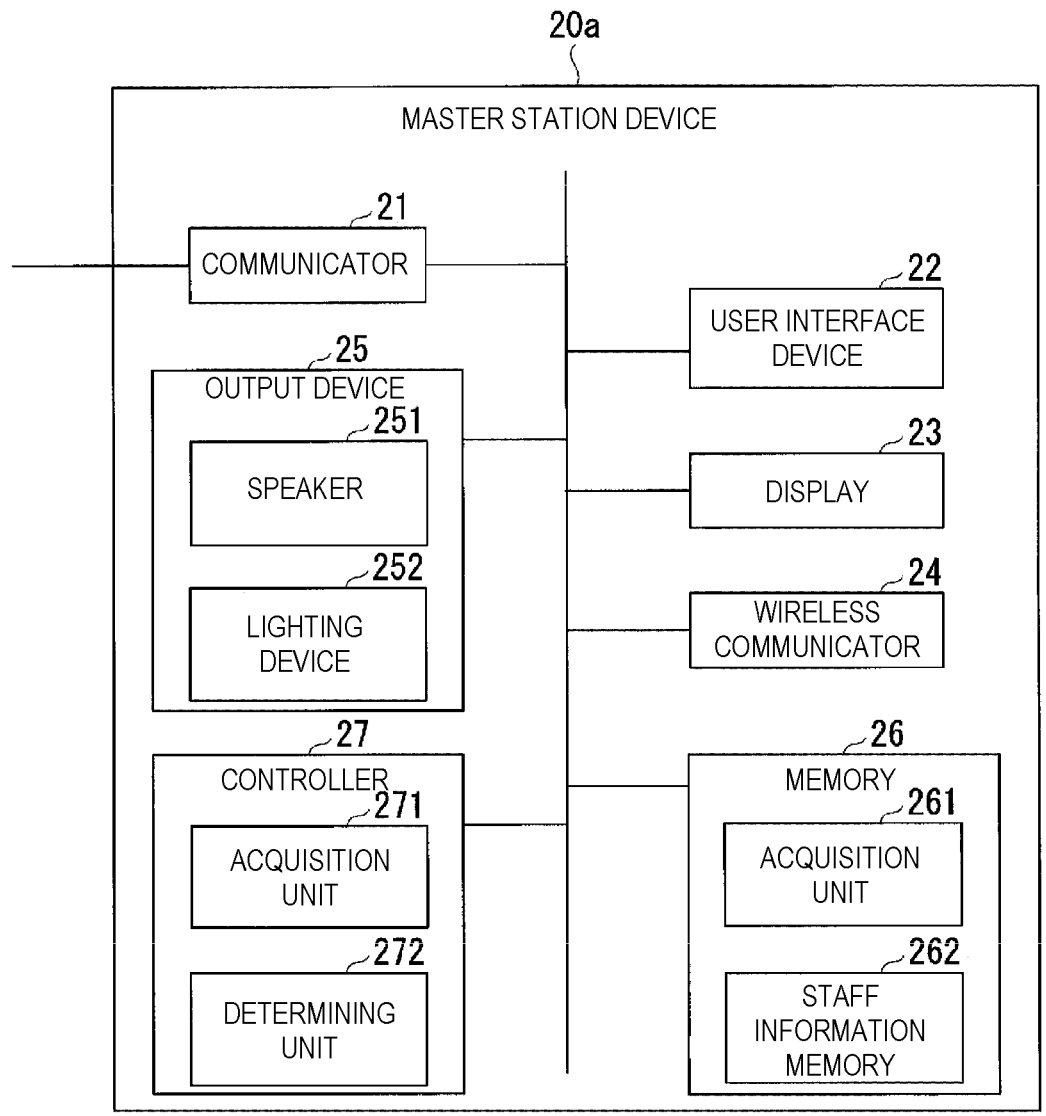
[Fig. 10]
| STAFF IDENTIFICATION INFORMATION | MOVABLE TERMINAL IDENTIFICATION INFORMATION |
|---|---|
|  |  |
|  |  |
|  |  |
|  |  |
72

[Fig. 11]
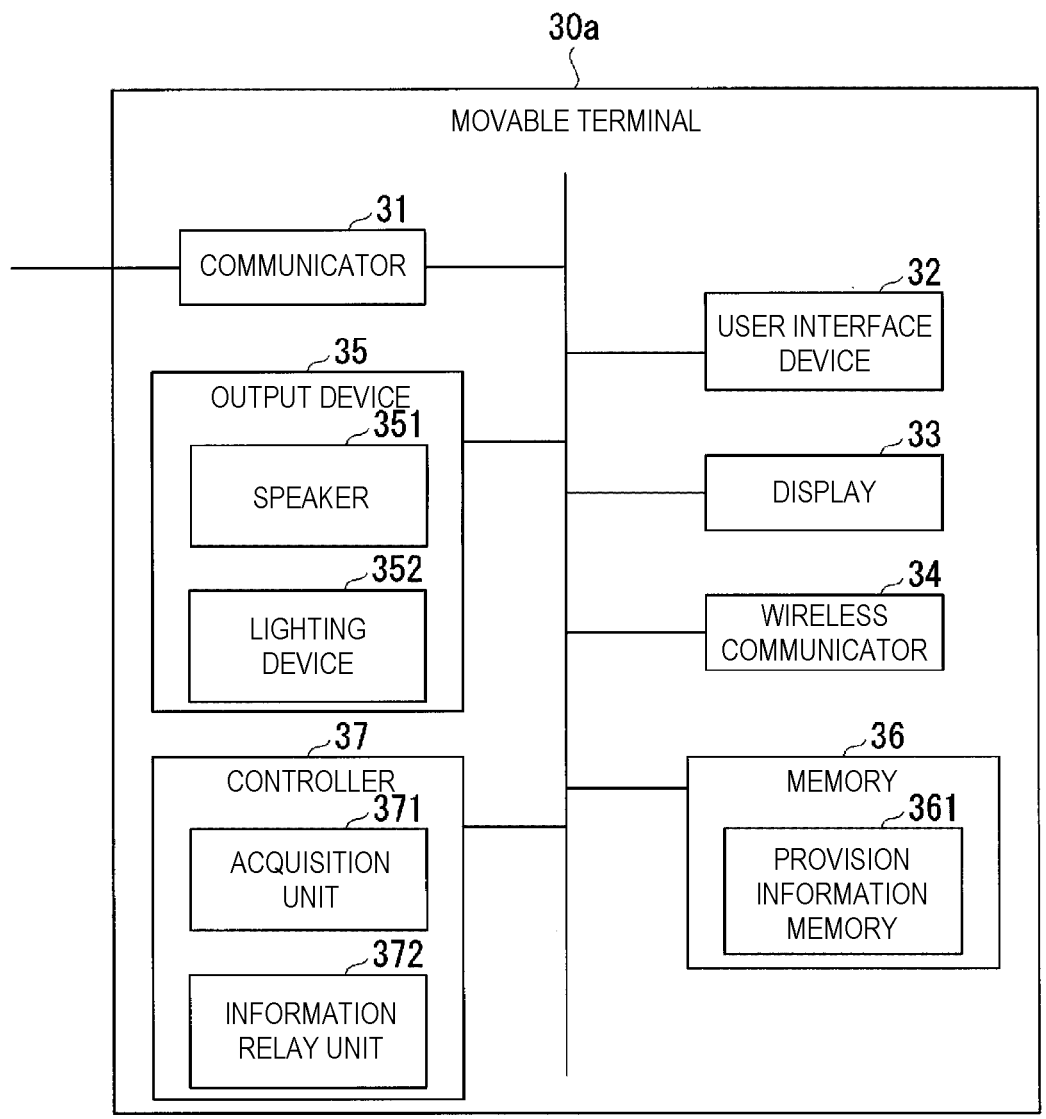

[Fig. 12]
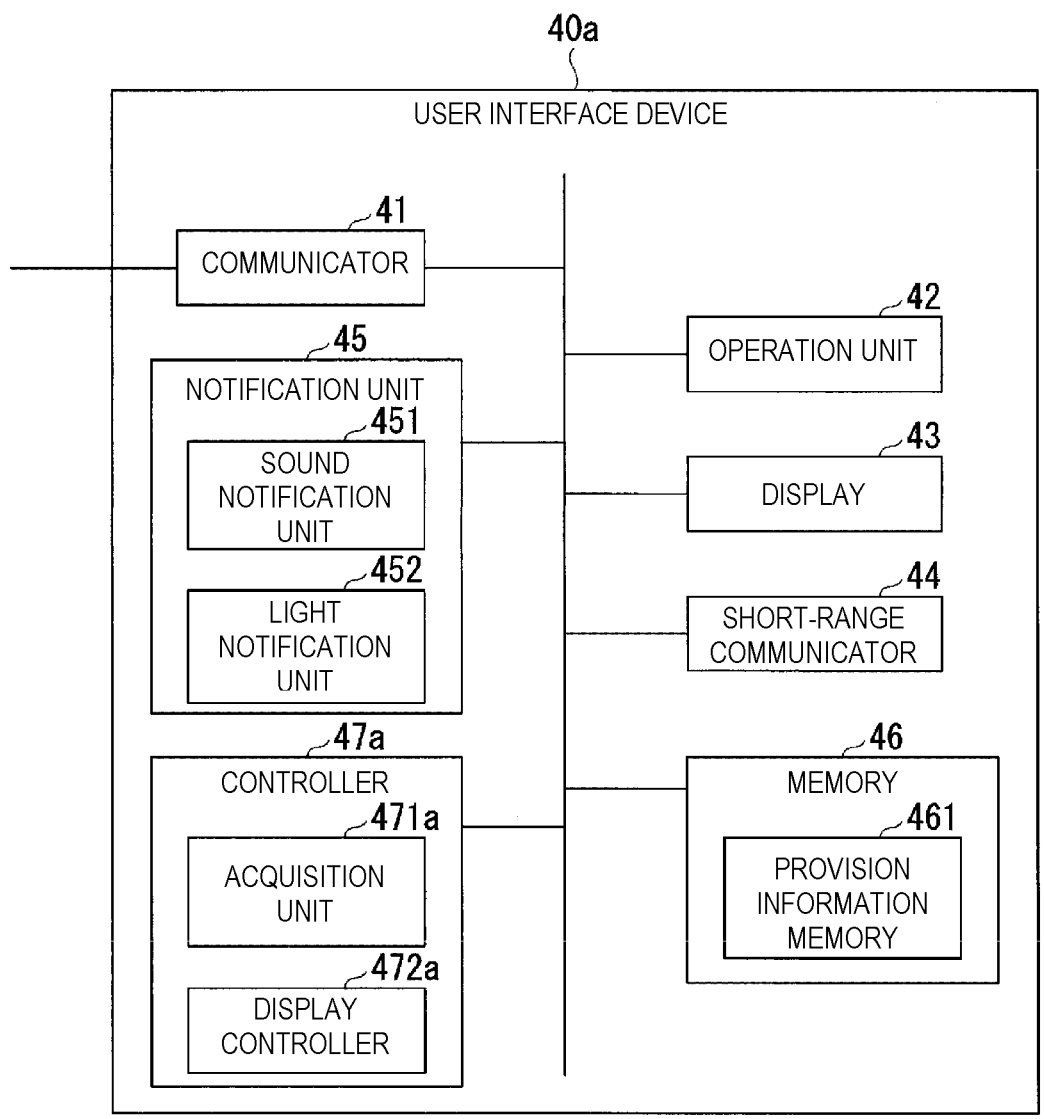

TERMINAL DEVICE, INFORMATION PROVIDING SYSTEM, AND COMPUTER PROGRAM

TECHNICAL FIELD

The present invention relates to a technique of providing information to a person who undergoes medical treatment or care.

This application claims the priority, based on the Japanese patent Application No. 2016-227222, filed on Nov. 22, 2016, the contents of which are incorporated herein by reference.

BACKGROUND ART

Conventionally, there are terminal devices that are arranged near the beds in the hospital, and provides various information to patients and medical treatment staffs (see PTL 1). The terminal device receives information from an information processing device such as a server that is connected thereto via a network. The terminal device displays the received information, thereby providing the information to the patients and the medical treatment staffs.

CITATION LIST

Patent Literature

PTL 1: JP-A-2002-041671

SUMMARY OF INVENTION

Technical Problem

However, when the terminal device is unable to acquire the latest information because of a matter such as a trouble occurring in the network or in the information processing device, information that is not the latest (hereinafter, referred to as "old information") may be provided in some cases. The old information may include unsuitable information due to the oldness thereof in some cases. Such a problem is not only a problem limited to a case where the terminal device is used in the hospital, but also is a problem common to a case where the terminal device is used in a facility such as a care facility that provides care service to care receivers.

In view of the abovementioned circumstances, an object of the invention is to provide a technique capable of suppressing unsuitable information from being provided, on a display device used for medical treatment or care.

Solution to Problem (1) A terminal device according to one aspect of the invention includes: an acquisition unit that receives information to be displayed on a display device used for medical treatment or care from a server, and stores the received information in a memory; and a display controller that causes the display device to display the information, in which when a display stop condition as a condition indicating a likelihood that a difference occurs between information stored in the server and information stored in the memory is satisfied, the display controller stops display of at least information related to biological information on a facility user who is a subject of the medical treatment or the care, among the information on the display device.

(2) In the terminal device of (1), when a display resume condition as a condition indicating that the information stored in the memory has been updated to the information stored in the server is satisfied after the display controller stops the display of the information on the display device, the display controller may resume the display of the information on the display device.

(3) A terminal device according to another aspect of the invention includes: an acquisition unit that receives information to be displayed on a display device used for medical treatment or care from a server, and stores the received information in a memory; and a display controller that causes the display device to display the information, in which when a display stop condition as a condition indicating a likelihood that a difference occurs between a state indicated by information stored in the memory and an actual state related to the medical treatment or the care is satisfied, the display controller stops display of at least information related to biological information on a facility user who is a subject of the medical treatment or the care, among the information on the display device.

(4) In the terminal device of any one aspect of (1) to (3), the information may be information that is provided to the facility user or a staff who provides the medical treatment or the care to the facility user, and the display device may be a device that is visible to the facility user.

(5) In the terminal device of any one aspect of (1) to (4), when a prescribed condition is satisfied in a state where the display stop condition is satisfied, the display controller may display the information stored in the memory in a mode of indicating that information being displayed may be old.

(6) An information providing system according to one aspect of the invention includes: the terminal device of any one aspect of (1) to (5); and a determining unit that transmits the information to relay information equipment that is information equipment carried by a person who is highly likely to visit a room where the terminal device is installed, in which the determining unit is provided in an information processing device different from the terminal device.

(7) A computer program according to one aspect of the invention causes an information processing device to function as a terminal device, the terminal device including: an acquisition unit that receives information to be displayed on a display device used for medical treatment or care from a server, and stores the received information in a memory; and a display controller that causes the display device to display the information, in which when a display stop condition as a condition indicating a likelihood that a difference occurs between information stored in the server and information stored in the memory is satisfied, the display controller stops display of at least information related to biological information on a facility user who is a subject of the medical treatment or the care, among the information on the display device.

Advantageous Effects of Invention

With the abovementioned respective aspects of the invention, it is possible to suppress unsuitable information from being provided, on the display device used for medical treatment or care.

BRIEF DESCRIPTION OF THE DRAWINGS

FIG. 1 is a diagram illustrating an example of a system configuration of an information providing system (information providing system 1) according to a first embodiment of the invention.

FIG. 2 is a schematic block diagram illustrating a function configuration example of a server 10.

FIG. 3 is a diagram illustrating a specific example of a facility user information table.

FIG. 4 is a diagram illustrating a specific example of electronic medical record data.

FIG. 5 is a schematic block diagram illustrating a function configuration example of a user interface device 40.

FIG. 6 is a diagram illustrating one example of an appearance of the user interface device 40.

FIG. 7 is a diagram illustrating an example of an operation of a display controller 472 of the user interface device 40.

FIG. 8 is a diagram illustrating an example of a system configuration of an information providing system (information providing system 1a) according to a second embodiment.

FIG. 9 is a schematic block diagram illustrating a function configuration example of a master station device 20a.

FIG. 10 is a diagram illustrating a specific example of a staff information table.

FIG. 11 is a schematic block diagram illustrating a function configuration example of a terminal device 30a.

FIG. 12 is a schematic block diagram illustrating a function configuration example of a user interface device 40a.

DESCRIPTION OF EMBODIMENTS

First Embodiment

FIG. 1 is a diagram illustrating an example of a system configuration of an information providing system (information providing system 1) according to a first embodiment. The information providing system 1 is provided in a facility such as a hospital or a care facility where a person as a subject for medical treatment or care (hereinafter, referred to as "facility user") stays (including hospitalization) or lives. The information providing system 1 provides information to the facility user.

In the information providing system 1, a facility user P lies down on a mattress 52 that is placed on a bed 50. A detection device 53a is provided on the bed 50. The detection device 53a is connected to a user interface device 40. The detection device 53a may be installed between sections 51 and the mattress 52 for example. The sections constitute the bed 50. The detection device 53a is one specific example of a sensor 53, which is described later.

The user interface device 40 is connected to the detection device 53a, is connected to measuring devices 60 (for example, devices including a clinical thermometer and a sphygmomanometer), and is connected to a remote server 70 via a network. An ID card 65 is held up over the user interface device 40 to allow an authentication process (login process) to be implemented.

For example, a server 10, a master station device 20, a plurality of terminal devices 30, and the remote server 70 are connected to the network. The server 10, the master station device 20, and the terminal device 30 will be described later in details. The remote server 70 is a server that provides various kinds of service, and is externally provided via the Internet.

The information providing system 1 is described again. The information providing system 1 is provided with the server 10, the master station device 20, a plurality of the terminal device 30, a plurality of the user interface devices 40, and a plurality of the sensors 53. The user interface device 40 is installed in a room where the facility user P stays or lives. For example, one user interface device 40 is associated with one facility user P. Information is displayed on a display of the user interface device 40 to provide the information to the facility user P and the staff. The sensor 53 is connected to the user interface device 40 directly or via another device (for example, a control box provided to the bed 50). The communication between the user interface device 40 and the sensor 53 may be wired communication or wireless communication. The sensor 53 measures biological information on the facility user P, and outputs a measurement result directly or via another device to the user interface device 40. This enables the user interface device 40 to acquire in real time the biological information on the facility user P. Information is displayed on the display of the user interface device 40 to provide the information to the facility user P. The sensor 53 is not necessarily directly connected to the user interface device 40. The sensor 53 may be connected to the user interface device 40 via the bed 50, for example.

The server 10 is connected to other respective devices by wired communication or wireless communication so as to allow communication therewith. A part or all of communication paths between the server 10 and the other respective devices may be common, or may be independent of one another.

The server 10 includes a communicable information processing device. The server 10 is communicable with the master station device 20, the plurality of terminal devices 30, and the plurality of user interface devices 40 via the communication paths. The server 10 is provided with a central processor unit (CPU), a memory, and an auxiliary storage device, which are connected with a bus. The server 10 operates by executing a stored program. The server 10 stores therein electronic medical record data. The server 10 transmits, in response to a request from another device, electronic medical record data that the own device stores therein, to the device that is a request source.

FIG. 2 is a schematic block diagram illustrating a function configuration example of the server 10. The server 10 is provided with a communicator 11, a memory 12, and a controller 13.

The communicator 11 includes a communication interface device. The communicator 11 communicates with another device via the wireless communication or the wired communication. The communicator 11 communicates with, for example, the master station device 20, the terminal device 30, and the user interface device 40.

The memory 12 includes a storage device such as a magnetic hard disk device or a semiconductor memory device. The memory 12 functions as a provision information memory 121, a facility user information memory 122, and an electronic medical record data memory 123. A part or all of information that the memory 12 stores therein is controlled so as to be readable with respect to the master station device 20 or the terminal device 30. For example, information that the facility user information memory 122 and the electronic medical record data memory 123 respectively store therein may be controlled so as to be readable from the master station device 20 or the terminal device 30.

The provision information memory 121 stores therein provision information acquired by the controller 13. The provision information is information that is displayed in the user interface device 40, and thus is provided to users (the facility user P and the staff) of the user interface device 40.

The facility user information memory 122 stores therein facility user information. The facility user information memory 122 may store therein, for example, a facility user information table as facility user information. FIG. 3 is a diagram illustrating a specific example of a facility user information table. The facility user information table includes a plurality of facility user information records 71. Each facility user information record 71 includes respective values of facility user identification information, user interface device identification information, and attribute information.

The facility user identification information is identification information uniquely indicating the facility user P who stays or lives in a facility where the information providing system 1 is installed. The user interface device identification information is identification information uniquely indicating the user interface device 40 that is provided in the information providing system 1. The user interface device identification information includes identification information on the user interface device 40 that is allocated to the facility user P indicated by the facility user identification information of the same facility user information record 71. The attribute information is information related to the facility user P. The attribute information includes, for example, a gender of the facility user P, an age of the facility user P, and an address of the facility user P. The attribute information includes attribute information related to the facility user P indicated by the facility user identification information of the same facility user information record 71.

The electronic medical record data memory 123 stores therein electronic medical record data. FIG. 4 is a diagram illustrating a specific example of electronic medical record data. In the electronic medical record data, for each facility user P, information on a medical record related to each facility user P is registered. For example, the electronic medical record data includes medical information 81, caution information 82, and biological information 83.

The medical information 81 includes information related to medical care that the facility user P undergoes, and information related to the facility user P who undergoes the medical care. For example, the medical information 81 includes the facility user identification, and each information on a name, a doctor in charge, a doctor attending, a nurse in charge, a diagnosis and treatment department, a room number, or a bed number. The medical information 81 may include information different from the above-described information. For example, the medical information 81 may include information related to a disease from which the facility user P suffers, information related to medical treatment or care that is conducted with respect to the facility user P, information related to equipment that is used with respect to the facility user P, information related to hospitalization of the facility user P (hospitalization date, length of hospital stay, expected date of hospital discharge, and the like), status information on the facility user P (during the hospitalization procedure, during hospitalization, during surgery, during the hospital discharge procedure, already hospital discharged, and the like), and information related to a medicine that is administered with respect to the facility user P. Care information, in place of the medical information 81, may be registered with the electronic medical record data. The care information includes information with the same intent as the medical information 81. For example, the care information may include information related to the facility user P who undergoes the care (facility user identification information, a name, a doctor attending, a care worker in charge, a room number, a bed number, and the like).

The caution information 82 includes information to which a person who conducts medical treatment or care (hereinafter, referred to as "staff") needs to pay attention. The caution information 82 includes, for example, information related to notify caution or information related to risk assessments. Specific examples of the information related to notify caution include, regular collection of blood (indicating that collection of blood needs to be conducted at predetermined time), prohibition of nose blowing (indicating that an act of nose blowing needs to be prohibited), and use of air mattress (indicating that the normality of the air mattress needs to be checked). Specific examples of the information related to risk assessments include, bedsore caution (bedsore assessment) and fall caution (fall assessment). The caution information 82 may be registered as a pictogram.

The biological information 83 is biological information that is measured about the facility user P. In the example of FIG. 4, a measurement result of each biological information is registered in association with the measurement date/time. Specific examples of the biological information include a pulse, a systolic blood pressure, a diastolic blood pressure, and a body temperature. The biological information to be registered with the electronic medical record data is not necessarily limited to the items illustrated in FIG. 4. Specific examples of another biological information include values of a blood glucose level, a respiratory rate, a body weight, a body height, a body fat, and the like.

The description returns to the explanation for FIG. 2. The controller 13 includes a CPU. The controller 13 executes the stored program to function as an acquisition unit 131, an information providing unit 132, and an electronic medical record controller 133.

The acquisition unit 131 acquires provision information. The acquisition unit 131 may acquire provision information with any means. For example, the acquisition unit 131 may acquire information that is input with an input device such as a key board connected to the own device (the server 10), as provision information. For example, the acquisition unit 131 may receive provision information from another information processing device via the network. For example, the acquisition unit 131 may read provision information that is recorded on an external memory unit such as a universal serial bus (USB) memory or a recording medium such as a CD-ROM. The acquisition unit 131 stores the acquired provision information in the provision information memory 121. The acquisition unit 131 may store, when storing provision information in the provision information memory 121, the date/time when the provision information was acquired in association with each provision information.

The information providing unit 132 transmits provision information that is stored in the provision information memory 121, to each user interface device 40 that is provided in the information providing system 1. The information providing unit 132 may transmit the provision information to all the user interface devices 40, or may transmit the provision information only to the user interface device 40 of the facility user P to whom the provision information is needed to be provided. The information providing unit 132 may determine the user interface device 40 that is a destination of transmission, on the basis of information indicating the facility user P as a provision subject that is included in the provision information (hereinafter, referred to as "provision subject information"), for example. The following describes more specifically.

The provision subject information is, for example, facility user identification information on the facility user P as a provision subject, information indicating a room where the facility user P as a provision subject stays or lives, and information indicating medical treatment or care that is conducted with respect to the facility user P as a provision subject. Such information specifies the facility user P who is a provision subject. The information providing unit 132 searches, for example, the facility user information record 71 including attribute information that coincides with the provision subject information. The information providing unit 132 determines the user interface device 40 indicated by user interface device identification information of the searched facility user information record 71, to be the user interface device 40 that is a destination of transmission of the provision information. The information providing unit 132 searches, for example, electronic medical record data including a value that coincides with the provision subject information. The information providing unit 132 determines the user interface device 40 corresponded to the facility user P of the searched electronic medical record data, to be the user interface device 40 that is a destination of transmission of the provision information. Which user interface device 40 is the user interface device 40 corresponded to the facility user P can be determined by referring to the facility user information record 71.

The electronic medical record controller 133 executes necessary processing in order that the server 10 functions as an electronic medical record server. When acquiring information related to the facility user P from another device, the electronic medical record controller 133 updates electronic medical record data on the basis of the acquired information. When receiving a request for information that is registered with the electronic medical record data from another device, the electronic medical record controller 133 reads the information from the electronic medical record data memory 123 in response to the request. The electronic medical record controller 133 then transmits the read information to the device as a request source.

The description returns to the explanation for FIG. 1. The master station device 20 includes a communicable information processing device. The master station device 20 is communicable with the server 10 via the communication path. The master station device 20 is provided with a CPU, a memory, and an auxiliary storage device, which are connected to one another with a bus. The master station device 20 operates by executing a program. The master station device 20 may be installed at a place such as a nurse station where at least one staff is standby. The master station device 20 displays information related to the facility user P in a room that is positioned within a prescribed region (for example, on the same floor or in the same ward), or information related to equipment that is installed in the prescribed region. The staff can acquire information related to the facility user P, information related to equipment, or electronic medical record data of the facility user P by operating the master station device 20.

The terminal device 30 is portable, and includes a communicable information processing device. The terminal device 30 may include a device such as a smartphone, a mobile telephone set, a tablet terminal, and a portable dedicated terminal. The terminal device 30 is communicable with the server 10 via the communication path. The terminal device 30 is provided with a CPU, a memory, and an auxiliary storage device, which are connected to one another with a bus. For example, a staff carries the terminal device 30. The terminal device 30 displays information related to the facility user P or information related to equipment. The staff can acquire information related to the facility user P or information related to equipment by operating the terminal device 30.

The user interface device 40 includes a communicable information processing device. The user interface device 40 is communicable with the server 10 via the communication path. The user interface device 40 is provided with a CPU, a memory, and an auxiliary storage device, which are connected to one another with a bus. The user interface device 40 operates by executing a user interface device program. The user interface device 40 is installed, for example, near the bed 50, on a wall surface, near an entrance, on a table, or the like, in the room of the facility user P. The user interface device 40 displays information related to the facility user P in the room where the own device is installed or provision information that is provided to the facility user P in the room where the own device is installed. Users of the user interface device 40 (the facility user P and the staff) can watch provision information displayed on the user interface device 40.

FIG. 5 is a schematic block diagram illustrating a function configuration example of the user interface device 40. The user interface device 40 is provided with a communicator 41, a user interface device 42, a display 43, a wireless communicator 44, an output device 45, a memory 46, and a controller 47.

The communicator 41 includes a communication interface device. The communicator 41 communicates with another device via the wireless communication or the wired communication. The communicator 41 communicates with the server 10, for example.

The user interface device 42 includes an existing input device such as a keyboard, a pointing device (a mouse, a tablet, or the like), a button, or a touch panel. The user operates the user interface device 42, when inputting an instruction by the user to the user interface device 40. The user interface device 42 may be an interface for connecting the input device to the user interface device 40. In this case, the user interface device 42 inputs an input signal generated in response to an input by the user in the input device, to the user interface device 40. The user interface device 42 may be configured as a touch panel integrated with the display 43. The users herein indicate the facility user P and the staff.

The display 43 is an image display device such as a cathode ray tube (CRT) display, a liquid crystal display, or an organic electro luminescence (EL) display. The display 43 displays an image or characters. The display 43 may be an interface for connecting the image display device to the user interface device 40. In this case, the display 43 generates a video signal for displaying an image or characters, and outputs the video signal to the image display device that is connected to the display 43 itself.

The wireless communicator 44 communicates with another equipment that is positioned near the user interface device 40. A communication method to be used by the wireless communicator 44 may be wireless communication or may be wired communication. Specific examples of the wireless communication method used by the wireless communicator 44 include, near field communication (NFC), Bluetooth (registered trademark), TransferJet (registered trademark), ZigBee (registered trademark), RFID, and a wireless LAN. Specific examples of the wired communication method used by the wireless communicator 44 include a universal serial bus (USB), a wired LAN, a cable of a unique protocol, and RS-232C.

The wireless communicator 44 may communicate with an ID card carried by the staff, for example. In this case, the wireless communicator 44 acquires information used for authentication (hereinafter, referred to as "authentication information") from the ID card, by the communication. The wireless communicator 44 outputs authentication information to a function (authentication controller, which is not illustrated) that authenticates the staff on the basis of the authentication information. The wireless communicator 44 may communicate with a device that measures biological information on the facility user P or information related to the facility user P such as position information, for example. The position information is information indicating the current position or a history of the past position. In this case, the wireless communicator 44 acquires information related to the facility user P such as biological information and position information, by the communication.

The output device 45 operates when notifying a person who is positioned near the user interface device 40 of some information. The output device 45 functions as a speaker 451 and a lighting device 452.

The speaker 451 includes speakers. The speaker 451 emits sound in accordance with control by the controller 47. The speaker 451 emits, for example, a preset alarm to notify a person positioned in the vicinity of the occurrence of an event that requires caution.

The lighting device 452 includes a light emitting device. The lighting device 452 emits light in accordance with control by the controller 47. The lighting device 452 may light up, may blink on a prescribed cycle, or emit light in another mode, for example. The lighting device 452 emits, for example, light in a preset mode to notify a person positioned in the vicinity of the occurrence of an event that requires caution.

The memory 46 includes a storage device such as a magnetic hard disk device or a semiconductor memory device. The memory 46 functions as a provision information memory 461. The provision information memory 461 stores therein provision information to be acquired by the controller 47.

The controller 47 includes a CPU. The controller 47 executes a stored program to function as an acquisition unit 471 and a display controller 472.

The acquisition unit 471 acquires provision information from the server 10 via the communication path. The acquisition unit 471 causes the provision information memory 461 to store therein the acquired provision information. The acquisition unit 471 may cause, when causing the provision information memory 461 to record the provision information, the provision information memory 461 to record the acquired date/time in association with each provision information.

The display controller 472 controls the display 43. The display controller 472 reads the latest provision information from the provision information memory 461, for example, and causes the display 43 to display thereon an image illustrating the read provision information.

FIG. 6 is a diagram illustrating one example of an appearance of the user interface device 40. The user interface device 40 may include a plurality of separate housings, as illustrated in FIG. 6. For example, the user interface device 40 may be provided with a display 410 and a terminal device 420. The display 410 is provided with the communicator 41, the user interface device 42, the display 43, the output device 45, the memory 46, and the controller 47. The terminal device 420 is provided with the wireless communicator 44. The display 410 and the terminal device 420 may be connected so as to allow communication using, for example, terminals that are contacted with each other contact, or may be connected so as to allow communication by the wireless communication. The above-described configurations of the display 410 and the terminal device 420 are merely examples, so that configurations respectively different from the above-described configurations may be employed. The display 410 and the terminal device 420 may be provided with an overlapped function. For example, both of the display 410 and the terminal device 420 may be provided with the configuration corresponding to the controller 47.

FIG. 7 is a diagram illustrating an example of an operation of the display controller 472 of the user interface device 40. The display controller 472 determines whether a preset display stop condition is satisfied (Step S101). The display stop condition is a condition indicating a likelihood that a difference occurs between information stored that is in the provision information memory 121 of the server 10 and information that is stored in the provision information memory 461 of the user interface device 40. If the display stop condition is satisfied, it can be presumed that provision information that is stored in the provision information memory 461 is old information. The display stop condition may be such a condition that the communication via the communicator 41 has not been normally executed, for example. More specifically, it may be a condition that a state where the controller 47 is unable to acquire communication data from the communicator 41 has been continued over a prescribed period. The display stop condition may be such a condition that a trouble occurs in a communication path with the server 10, for example. More specifically, it may be a condition that data (data for survival confirmation) that needs to be received from the server 10 at a prescribed timing has not been normally received. The display stop condition may be such a condition that the controller 47 is unable to acquire new provision information over a prescribed period, for example. The display stop condition may be such a condition that the facility user P related to the provision information is proceeding a hospital discharge procedure, for example. More specifically, the display stop condition may be a condition that status information that is registered with electronic medical record data of the facility user P related to the provision information is during the hospital discharge procedure. When the hospital discharge procedure is proceeding, the facility user P to whom the user interface device 40 is allocated is generally changed before and after the hospital discharge procedure, so that there is a possibility that the facility user P is not correctly allocated. Such a condition is set as a display stop condition to make it possible to prevent information related to the facility user P during the hospital discharge procedure from erroneously displaying on the user interface device 40.

If the display stop condition is not satisfied (Step S101—NO), the display controller 472 continues display on the display 43. In this case, the display controller 472 causes the display 43 to display a part or all of the content of the provision information, for example. On the other hand, if the display stop condition is satisfied (Step S101—YES), the display controller 472 stops display of the provision information on the display 43 (Step S102). In this process, the display controller 472 stops display of information related to at least biological information on the facility user P, among the provision information on the display 43. When the display controller 472 stops the display, an image or characters indicating that the display is sopped is displayed on the display 43. Such an image or characters may be displayed under the control by the display controller 472, or may be displayed under the control by the display 43. For example, the display controller 472 may generate a video signal indicating the abovementioned image or characters, and may output the video signal to the display 43. For example, the display 43 may display the abovementioned image or characters in response that the display controller 472 stops the output of the video signal to the display 43. When the display is stopped, neither of an image nor characters may be displayed on the display 43. The display controller 472 may be configured not to display information related to the facility user P with which the user interface device 40 is associated, when the display is stopped.

After stopping the display, the display controller 472 determines whether a display resume condition is satisfied (Step S103). The display resume condition is a condition indicating that the provision information that is stored in the provision information memory 461 has been updated to the latest information. If the display resume condition is satisfied, it can be presumed that the provision information that is stored in the provision information memory 461 has been updated to the latest information. The display resume condition may be such a condition that the normal execution of the communication via the communicator 41 has become possible, for example. More specifically, it may be such a condition that the controller 47 has become possible to acquire communication data from the communicator 41. The display resume condition may be such a condition that the trouble having occurred in the communication path with the server 10 has recovered, for example. More specifically, it may be a condition that data (data for survival confirmation) that needs to be received from the server 10 at a prescribed timing has been normally received. The display resume condition may be such a condition that the controller 47 has become possible to acquire new provision information, for example. The display resume condition may be such a condition that an operator having a prescribed authority has input an instruction to resume display with the user interface device 42. The controller 47 may determine whether the prescribed authority is present on the basis of the authentication information received via the wireless communicator 44, for example. The operator having a prescribed authority is, for example, among the staffs, a person (for example, a doctor in charge, a doctor attending, or a nurse in charge) in charge of medical treatment or care for the facility user P to whom the user interface device 40 is allocated.

If the display resume condition is not satisfied (Step S103—NO), the display controller 472 remains the display on the display 43 stopped. On the other hand, if the display resume condition is satisfied (Step S103—YES), the display controller 472 resumes the display on the display 43 (Step S104). When the display controller 472 resumes display, a screen that is displayed in normal times is displayed on the display 43. For example, the screen having been displayed before the display is stopped at Step S102 may be displayed on the display 43. In this case, newly acquired provision information may be displayed in a region where the provision information is displayed within the displayed screen.

In the information providing system 1 configured in this manner in the first embodiment, it is possible to suppress unsuitable information from providing to a person who undergoes medical treatment or care (the facility user P). The following describes in details.

In the information providing system 1 in the first embodiment, when a condition indicating (display stop condition) that a difference occurs between provision information stored in the server 10 and provision information stored in the user interface device 40 is satisfied, the display on the display 43 is stopped. In such a case, it is inappropriate to provide the provision information that is stored in the user interface device 40 to the facility user P because there is a possibility that the provision information stored in the user interface device 40 may include an error content. The display controller 472 of the user interface device 40 operates in the abovementioned manner, so that it is possible to suppress the provision information having a possibility of being old from being provided to the facility user P.

In the information providing system 1 in the first embodiment, when a condition (display resume condition) indicating that the provision information is updated to the latest information is satisfied after the display stop condition is satisfied and the display is stopped, the display on the display 43 is resumed. This makes it possible to rapidly provide the updated latest provision information to the facility user P.

Modification Example

The number of the master station devices 20 included in the information providing system 1 is not limited to one. A plurality of the master station devices 20 may be provided.

The server 10 may be mounted on a plurality of devices by the function thereof being separated thereto. For example, the electronic medical record data memory 123 and the electronic medical record controller 133 may be mounted to another device as an electronic medical record server.

Although the configuration in which the user interface device 40 is installed in a room where the facility user P stays or lives and one user interface device 40 is associated with one facility user P is described in the present embodiment, one user interface device 40 may be commonly used by a plurality of the facility users P or may be installed in a path such as a corridor.

The output device 45 may be provided with an output device having a mode different from the speaker 451 and the lighting device 452. For example, the information providing system 1 may be provided with an output device that makes a notification by generating vibration, or may be provided with an output device that makes a notification by moving a movable part. The output device 45 is not necessarily provided with both of the speaker 451 and the lighting device 452. The output device 45 may be provided with either one of the speaker 451 and the lighting device 452.

In a case of a display stop state (state where the display stop condition is satisfied), the display controller 472 may display prescribed information if a prescribed condition is satisfied. For example, when the staff logs in the user interface device 40 (prescribed condition), the display controller 472 may display information on the facility user P (for example, patient) with which the user interface device 40 is associated. In this case, the display controller 472 may display information in a mode indicating that there is a possibility that the displayed information is old. Specific examples of such display modes include a mode of displaying information by changing the background color, a mode of displaying characters or an image (pictogram) indicating the display stop state, and a mode of displaying the time when the information being displayed is acquired for the last time or the time when the information being displayed is updated for the last time.

The display stop condition may be defined as a condition indicating a likelihood that a difference occurs between a state indicated by the information that is stored in the memory 12 and an actual state related to medical treatment or care. For example, such a case may occur that in the facility user information memory 122 of the memory 12, when identification information on a facility user called "A" is registered, the facility user called "A" is no longer a facility user due to circumstances such as a hospital discharge. In such a case, even when no difference occurs between information that is stored in the server 10 and information that is stored in the memory 12, it may be determined that the display stop condition is satisfied. Such a determination may be made, for example, based on whether a staff in charge of the hospital discharge procedure has performed a prescribed operation with respect to the user interface device 42 of the user interface device 40 related to a facility user who is going to leave the hospital or has already left the hospital. The prescribed operation may include a button indicating the hospital discharge being pressed, for example.

Second Embodiment

FIG. 8 is a diagram illustrating an example of a system configuration of an information providing system (information providing system 1a) according to a second embodiment. The information providing system 1a has a configuration partially different from the information providing system (the information providing system 1) in the first embodiment. Hereinafter, the second embodiment (the information providing system 1a), specially a point different from the first embodiment, will be described.

The information providing system 1a is provided with the server 10, a master station device 20a, a plurality of terminal devices 30a, and a plurality of user interface devices 40a. The configuration of the server 10 in the second embodiment is the same as the server 10 in the first embodiment, so that an explanation thereof is omitted.

The master station device 20a includes a communicable information processing device. The master station device 20a is communicable with the server 10 via the communication path. The master station device 20a is provided with a CPU, a memory, and an auxiliary storage device, which are connected to one another with a bus.

FIG. 9 is a schematic block diagram illustrating a function configuration example of the master station device 20a. The master station device 20a is provided with a communicator 21, a user interface device 22, a display 23, a wireless communicator 24, an output device 25, a memory 26, and a controller 27.

The communicator 21 includes a communication interface device. The communicator 21 communicates with another device via the wireless communication or the wired communication. The communicator 21 communicates with the server 10, for example.

The user interface device 22 includes an existing input device such as a keyboard, a pointing device (a mouse, a tablet, or the like), a button, or a touch panel. The user operates the user interface device 22 when inputting an instruction by the user to the master station device 20a. The user interface device 22 may be an interface for connecting the input device to the master station device 20a. In this case, the user interface device 22 inputs an input signal that is generated in response to an input by the user in the input device, to the master station device 20a. The user interface device 22 may be configured as a touch panel integrated with the display 23.

The display 23 is an image display device such as a CRT display, a liquid crystal display, or an organic EL display. The display 23 displays an image or characters. The display 23 may be an interface for connecting the image display device to the master station device 20a. In this case, the display 23 generates a video signal for displaying an image or characters, and outputs the video signal to the image display device that is connected to the display 23 itself.

The wireless communicator 24 communicates with another equipment that is positioned in the vicinity of the master station device 20a.

A communication method to be used by the wireless communicator 24 may be wireless communication or may be wired communication. Specific examples of the wireless communication method used by the wireless communicator 24 include, NEC, Bluetooth (registered trademark), TransferJet (registered trademark), ZigBee (registered trademark), RFID, and a wireless LAN. Specific examples of the wired communication method used by the wireless communicator 24 include a USB, a wired LAN, a cable of a unique protocol, and RS-232C.

The wireless communicator 24 may communicate with an ID card carried by the staff, for example. In this case, the wireless communicator 24 acquires authentication information from the ID card, by the communication. The wireless communicator 24 outputs authentication information to a function (authentication controller, which is not illustrated) that authenticates the staff on the basis of the authentication information. The wireless communicator 24 may communicate with the terminal device 30a, for example. In this case, the wireless communicator 24 transmits, for example, provision information output from the controller 27 to the terminal device 30a.

The output device 25 operates when notifying a person who is positioned in the vicinity of the master station device 20a of some information. The output device 25 functions as a speaker 251 and a lighting device 252.

The speaker 251 includes speakers. The speaker 251 emits sound in accordance with control by the controller 27. The speaker 251 emits, for example, a preset alarm to notify a person positioned in the vicinity of the occurrence of an event that requires caution.

The lighting device 252 includes a light emitting device. The lighting device 252 emits light in accordance with control by the controller 27. The lighting device 252 may light up, may blink on a prescribed cycle, or emit light in another mode, for example. The lighting device 252 emits, for example, light in a preset mode to notify a person positioned in the vicinity of the occurrence of an event that requires caution.

The memory 26 includes a storage device such as a magnetic hard disk device or a semiconductor memory device. The memory 26 functions as a provision information memory 261 and a staff information memory 262.

The provision information memory 261 stores therein provision information acquired by the controller 27.

The staff information memory 262 stores therein staff information. The staff information memory 262 may store therein, for example, a staff information table as staff information. FIG. 10 is a diagram illustrating a specific example of a staff information table. The staff information table includes a plurality of staff information records 72. The staff information record 72 includes respective values of staff identification information and terminal device identification information.

The staff identification information is identification information uniquely indicating a staff. The terminal device identification information is identification information uniquely indicating the terminal device 30a. To the terminal device identification information, assigned is identification information on the terminal device 30a that is allocated to the staff indicated by the staff identification information of the same staff information record 72. The staff carries the terminal device 30a that is allocated to the staff him/herself. The staff information record 72 thus indicates a combination of the terminal device 30a and a staff who carries the terminal device 30a.

The description returns to the explanation for FIG. 9. The controller 27 includes a CPU. The controller 27 executes a dedicated program to function as an acquisition unit 271 and a determining unit 272.

The acquisition unit 271 acquires provision information from the server 10 via the communication path. The acquisition unit 271 causes the provision information memory 261 to store therein the acquired provision information. The acquisition unit 271 may cause, when causing the provision information memory 261 to record the provision information, the provision information memory 261 to record the date/time when the provision information was acquired in association with the provision information.

The determining unit 272 transmits provision information to relay information equipment through a communication path via the wireless communicator 24. In this process, the determining unit 272 may transmit provision information, together with identification information (for example, user interface device identification information) indicating the user interface device 40a that is a destination of the provision information. The relay information equipment is information equipment to relay provision information to the user interface device 40a (hereinafter, referred to as "relay destination terminal") that satisfies a condition indicating that the provision information is not updated. The relay information equipment is information equipment that is carried by a staff who is highly likely to visit a room where the relay destination terminal is installed. The determining unit 272 may transmit provision information, for example, to the terminal device 30a (relay information equipment) of a staff who is in charge of the facility user P to whom the relay destination terminal is allocated. In this case, the determining unit 272 may determine relay information equipment that is a transmission destination of the provision information on the basis of the staff information stored in the staff information memory 262. The following described a more specific example.

Firstly, the determining unit 272 determines the user interface device 40a that is a relay destination terminal. This determination is made based on whether a prescribed condition indicating that the provision information has not been updated yet is satisfied. For example, a determination may be made based on whether a condition indicating that normal communication has not been executed yet is satisfied. Specific examples of such a condition include the following conditions. For example, a condition may be such that data (data for survival confirmation) that needs to be transmitted from the user interface device 40a to the master station device 20a at the prescribed timing has not been received yet in the own device during the predetermined time or more. For example, a condition may be such that no response is made with respect to a response request (for example, ping) to be transmitted from the own device to the user interface device 40a at the prescribed timing.

The determining unit 272 determines the facility user P to whom the user interface device 40a determined to be a relay destination terminal is allocated, on the basis of information in the facility user information memory 122. The determining unit 272 determines a staff (for example, a doctor in charge, a doctor attending, or a nurse in charge) who is in charge of the determined facility user P, on the basis of information in the electronic medical record data memory 123. The determining unit 272 determines the terminal device 30a that is carried by the determined staff, on the basis of information in the staff information memory 262. The determining unit 272 determines such the terminal device 30a to be relay information equipment. Such processing is repeatedly executed at the prescribed timing.

Next, the terminal device 30a will be described. The terminal device 30a includes a communicable information processing device. The terminal device 30a is communicable with the server 10 via the communication path.

The terminal device 30a is provided with a CPU, a memory, and an auxiliary storage device, which are connected to one another with a bus.

FIG. 11 is a schematic block diagram illustrating a function configuration example of the terminal device 30a. The terminal device 30a is provided with a communicator 31, a user interface device 32, a display 33, a wireless communicator 34, an output device 35, a memory 36, and a controller 37.

The communicator 31 includes a communication interface device. The communicator 31 communicates with another device via the wireless communication or the wired communication. The communicator 31 communicates with the server 10, for example.

The user interface device 32 includes an existing input device such as a keyboard, a pointing device (a mouse, a tablet, or the like), a button, or a touch panel. A user operates the user interface device 32 when inputting an instruction by the user to the terminal device 30a. The user interface device 32 may be an interface for connecting the input device to the terminal device 30a. In this case, the user interface device 32 inputs an input signal that is generated in response to an input by the user in the input device, to the terminal device 30a. The user interface device 32 may be configured as a touch panel integrated with the display 33.

The display 33 is an image display device such as a CRT display, a liquid crystal display, or an organic EL display. The display 33 displays an image or characters. The display 33 may be an interface for connecting the image display device to the terminal device 30a. In this case, the display 33 generates a video signal for displaying an image or characters, and outputs the video signal to the image display device that is connected to the display 43 itself.

The wireless communicator 34 communicates with another equipment that is positioned in the vicinity of the terminal device 30a. A communication method to be used by the wireless communicator 34 may be wireless communication or may be wired communication. Specific examples of the wireless communication method used by the wireless communicator 34 include, NFC, Bluetooth (registered trademark), TransferJet (registered trademark), ZigBee (registered trademark), RFID, and a wireless LAN. Specific examples of the wired communication method used by the wireless communicator 34 include a USB, a wired LAN, a cable of a unique protocol, and RS-232C.

The wireless communicator 34 may communicate with an ID card carried by the staff, for example. In this case, the wireless communicator 34 acquires authentication information from the ID card, by the communication. The wireless communicator 34 outputs authentication information to a function (authentication controller, which is not illustrated) that authenticates the staff on the basis of the authentication information. The wireless communicator 34 may communicate with the master station device 20a, for example. In this case, the wireless communicator 34 receives provision information from the master station device 20a, for example.

The output device 35 operates when notifying a person who is positioned in the vicinity of the terminal device 30a (for example, a staff who carries the terminal device 30a) of some information. The output device 35 may make a notification that provision information is received from the master station device 20a, for example. The output device 35 functions as a speaker 351 and a lighting device 352. The configurations of the speaker 351 and the lighting device 352 are respectively the same as the configurations of the speaker 251 and the lighting device 252, which are provided in the master station device 20a. The explanations thereof are thus omitted.

The memory 36 includes a storage device such as a magnetic hard disk device or a semiconductor memory device. The memory 36 functions as a provision information memory 361.

The provision information memory 361 stores therein provision information that is acquired by the controller 37.

The controller 37 includes a CPU. The controller 37 executes a dedicated program to function as an acquisition unit 371 and an information relay unit 372.

The acquisition unit 371 acquires provision information from the master station device 20a via the wireless communicator 34. The acquisition unit 371 stores, in a provision information memory 361, the acquired provision information in association with identification information (user interface device identification information) on the user interface device 40a that is a provision destination of the provision information. The acquisition unit 371 may record, when recording provision information in the provision information memory 361, the date/time when the provision information was acquired in association with the provision information.

The information relay unit 372 transmits provision information to the user interface device 40a through a communication path via the wireless communicator 34. For example, when communication with the user interface device 40a indicated by user interface device identification information that is stored in association with provision information in the provision information memory 361 becomes possible, the information relay unit 372 transmits the provision information to the user interface device 40a. The information relay unit 372 may determine whether the communication is possible depending on whether prescribed information (for example, beacon including user interface device identification information) has been received via the wireless communicator 34, for example.

FIG. 12 is a schematic block diagram illustrating a function configuration example of the user interface device 40a. The user interface device 40a is different from the user interface device 40 in the first embodiment in that the user interface device 40a is provided with a controller 47a, in place of the controller 47. The configuration of the user interface device 40a other than the controller 47a is the same as that of the user interface device 40 in the first embodiment. The explanation of the configuration other than that of the controller 47a is omitted.

The controller 47a includes a CPU. The controller 47a executes a dedicated program to function as an acquisition unit 471a and a display controller 472a.

The acquisition unit 471a acquires provision information from the server 10 via the communication path. The acquisition unit 471a acquires provision information from the terminal device 30a via the wireless communicator 44. In both cases, the acquisition unit 471a causes the provision information memory 461 to store therein the acquired provision information.

The display controller 472a operates similarly to the display controller 472 in the first embodiment. The content of the display resume condition in the display controller 472 is partially different from the content of the display resume condition in the display controller 472 in the first embodiment. Hereinafter, a point different from the display controller 472 in the first embodiment will be described.

The display resume condition in the display controller 472a includes such a condition that provision information has been acquired via the wireless communicator 44. When provision information is acquired via the wireless communicator 44 after the display stop condition is satisfied, the display controller 472a determines that the display resume condition is satisfied, and resumes the display.

Even in a state where the display resume condition defined in the first embodiment is not satisfied, such a configuration makes it possible to resume the display in the user interface device 40a because provision information is acquired via the wireless communicator 44.

Modification Example

The information providing system 1a may be configured by modification similar to the first embodiment (the information providing system 1).

The output device 25 may be provided with an output device having a mode different from the speaker 251 and the lighting device 252. For example, the information providing system 1a may be provided with an output device that makes a notification by generating vibration, or may be provided with an output device that makes a notification by moving a movable part. The output device 25 is not necessarily provided with both of the speaker 251 and the lighting device 252. The output device 25 may be provided with either one of the speaker 251 and the lighting device 252. The same applies to the output device 35.

The server 10 may execute the processing of determining the user interface device 40a that is a relay destination terminal. In this case, the determining unit 272 receives information indicating the user interface device 40a that is a relay destination terminal from the server 10.

When the user interface device 40a that is a relay destination terminal is present, the determining unit 272 may cause the display 23 to display information indicating the user interface device 40a. When the user interface device 40a that is a relay destination terminal is present, the determining unit 272 determines a staff who carries information equipment determined to be relay information equipment, and may cause the display 23 to display information indicating the staff. Such the display being performed makes it possible to prompt the staff to manually update the provision information.

When communication with the relay information equipment via the wireless communicator 24 becomes possible, regardless of an operation by the staff, the determining unit 272 may transmit provision information to the relay information equipment. With such a configuration, provision information is automatically transmitted to the relay information equipment staff without the specific awareness of the staff.

The determining unit 272 may transmit only provision information that needs to be transmitted to the relay destination terminal, to the relay information equipment. The provision information that needs to be transmitted to the relay destination terminal is provision information to be provided to the facility user P to whom the relay destination terminal (the user interface device 40a) is allocated.

The function of the determining unit 272 may be provided not to the master station device 20a but to the server 10. In this case, with the function of the determining unit 272, the provision information is transmitted to the terminal device 30a not via the wireless communicator but via the communicator 11. The acquisition unit 371 of the terminal device 30a receives provision information via the communicator 31 from the server 10.

The information relay unit 372 may transmit provision information stored in the provision information memory 361 to all the user interface devices 40a that become communicable via the wireless communicator 34.

All or a part of the respective functions included in the respective devices in the above-described first embodiment and second embodiment may be implemented using hardware such as an application specific integrated circuit (ASIC), a programmable logic device (PLD), or a field programmable gate array (FPGA). The program executed by each of the above-described devices may be recorded on a computer-readable recording medium. Examples of the computer-readable recording medium include, for example, a portable storage medium such as a flexible disk, a magneto-optical disk, a ROM, or a CD-ROM, and a storage device such as a hard disk that is embedded in a computer system. Each program may be transmitted via an electric communication channel.

While the preferred embodiments of the invention have been described, the invention is not limited only to these embodiments and modifications thereof. Additions, omissions, substitutions, and changes of the configuration may be made without departing from the spirit of the invention.

Moreover, the invention is not limited by the above-described explanations, but is limited only by the accompanying claims.

INDUSTRIAL APPLICABILITY

With the abovementioned respective embodiments of the invention, it is possible to suppress unsuitable information from being provided, on the display device used for medical treatment or care.

REFERENCE SIGNS LIST 1, 1a: information providing system
10: server
11: communicator
12: memory
121: provision information memory
122: facility user information memory
123: electronic medical record data memory
13: controller
131: acquisition unit
132: information providing unit
133: electronic medical record controller
20, 20a: master station device
21: communicator
22: user interface device
23: display
24: wireless communicator
25: output device
251: speaker
252: lighting device
26: memory
261: provision information memory
262: staff information memory
27: controller
271: acquisition unit
272: determining unit
30, 30a: terminal device
31: communicator
32: user interface device
33: display
34: wireless communicator
35: output device
351: speaker
352: lighting device
36: memory
361: provision information memory
37: controller
371: acquisition unit
372: information relay unit
40, 40a: user interface device
41: communicator
42: user interface device
43: display
44: wireless communicator
45: output device
451: speaker
452: lighting device
46: memory
461: provision information memory
47, 47a: controller
471, 471a: acquisition unit
472, 472a: display controller
410: display
420: terminal device
50: bed
51: sections
52: mattress
53: sensor
60: measuring device
65: ID card
70: remote server
71: facility user information record
72: staff information record
81: medical information
82: caution information
83: biological information
P: facility user

The invention claimed is:

1. A user interface device comprising:
a wireless or wired communications interface configured to receive first information from an outside device, the first information including biological information;
a memory configured to store the received first information;
a display capable of displaying the stored first information; and
a controller, including a processor and a memory, the controller configured to stop displaying the stored first information on the display if a first condition is satisfied, the first condition indicating that the received first information stored in the memory has not been updated to a latest information.

2. The user interface device according to claim 1, wherein the controller is configured to continue displaying the stored first information on the display if the first condition isn't satisfied.

3. The user interface device according to claim 1, wherein the first information corresponds to information of a user who is a subject of the medical treatment.

4. The user interface device according to claim 1, wherein the controller is configured to again display the stored first information on the display device after stopping display of the stored first information on the display, if a second condition is satisfied, the second condition indicating that the received first information stored in the memory has been updated to the latest information.

5. The user interface device according to claim 4, wherein the controller is configured to continue to not display the stored first information on the display device, if the second condition is not satisfied.

6. The user interface device according to claim 1, wherein the controller is configured to display an image or characters indicating that the display of the first information is stopped on the display if the first condition is satisfied.

7. The user interface device according to claim 1, wherein part of the display is allocated to an area displaying the first information, and the controller is configured to display second information in the area if a second condition is satisfied.

8. A user interface device comprising:
 a wireless or wired communications interface configured to receive first information from an outside device, the first information including biological information;
 a memory configured to store the received first information;
 a display capable of displaying the stored first information; and
 a controller configured to stop displaying the stored first information on the display if a first condition is satisfied, the first condition indicating that a state indicated by the received first information stored in the memory and an actual state related to a medical treatment are different.

9. The user interface device according to claim 8, wherein the controller is configured to continue displaying the stored first information on the display if the first condition isn't satisfied.

10. The user interface device according to claim 8, wherein the first information corresponds to information of a user who is a subject of the medical treatment.

11. The user interface device according to claim 8, wherein the controller is configured to again display the stored first information on the display device after stopping display of the stored first information on the display, if a second condition is satisfied, the second condition indicating that the received first information stored in the memory has been updated to the latest information.

12. The user interface device according to claim 11, wherein the controller is configured to continue to not display the stored first information on the display device, if the second condition is not satisfied.

13. A system comprising:
 a master server including electronic medical record data of a user; and
 a user interface device including:
  a wireless or wired communications interface configured to receive first information from the master server, the first information including biological information,
  a memory configured to store the received first information;
  a display capable of displaying the stored first information; and
  a controller, including a processor and a memory, configured to stop displaying the stored first information on the display if a first condition is satisfied, the first condition indicating that the received first information stored in the memory has not been updated to a latest information.

14. The system according to claim 13, further comprising:
 a sensor configured to detect the biological information of the user on a condition that the sensor is provided between a bed and a mattress.

15. The system according to claim 14, wherein the sensor is capable of communicating with the user interface device.

16. The system according to claim 13, further comprising:
 a terminal device configured to transmit second information to an information equipment carried by a person who is highly likely to visit a room of the user, and
 wherein the information equipment is capable of transmitting the second information to the user interface device.

17. The system according to claim 15, further comprising:
 a terminal device configured to transmit second information to an information equipment carried by a person who is highly likely to visit a room of the user, and
 wherein the information equipment is capable of transmitting the second information to the user interface device.

* * * * *